United States Patent [19]
Hitz

[11] Patent Number: 5,846,784
[45] Date of Patent: Dec. 8, 1998

[54] **FATTY ACID MODIFYING ENZYMES FROM DEVELOPING SEEDS OF *VERNONIA GALAMENENSIS***

[75] Inventor: William D. Hitz, Wilmington, Del.

[73] Assignee: E. I. du Pont de Nemours and Company, Wilmington, Del.

[21] Appl. No.: 872,302

[22] Filed: Jun. 11, 1997

[51] Int. Cl.[6] .............................. C12N 9/02; C12N 15/53; C12N 15/10; C12N 15/63
[52] U.S. Cl. ...................... 435/91.2; 536/23.1; 536/232; 435/189; 435/172.3; 435/252.3; 435/320.1
[58] Field of Search .................................. 536/23.1, 23.2; 435/189, 91.2, 172.3, 252.3, 320.1

[56] References Cited

PUBLICATIONS

Ohlrogge, J.B., Plant Physiol., 104, 821–826, 1994.
Bafor, M. et al., Arch. Biochem. Biophys., 303, 145–151, 1993.
Shanklin, J. et al., Biochemistry, 33, 12787–12793, 1994.
Belanger, S.C. and Kriz, A.L., Plant Physiol., 91, 636–643, 1989.
Broun, P. and Somerville, C., Plant Physiol., 113, 933–942, 1997.
Adams, M.D. et al., Science, 252, 1651, 1991.
Van De Loo, F.J. et al., Proc. Natl. Acad. Sci., U.S.A. 92(15), 6743–6747, 1995.
Wallace, N.H. and Kriz, A.L., Plant Physiol., U.S.A., 95, 973–975, 1991.
Beachy et al., EMBO J., 4, 3047–3053, 1985.
Plant Physiol., vol. 110(1), Heppard et al., 1996, pp. 311–319.
Mol. Plant Microbe Interact., vol. 9(5), Gadea et al., 1996, pp. 409–415.
Genbank Accession L43921 (Oct. 1996).
Embl: Locus SCD12OLDS, Accession X92847 (Nov. 1995).
Embl: Locus LECEVI109G, Accession X94944 (Jul. 1996).

*Primary Examiner*—Rebecca E. Prouty

[57] ABSTRACT

This invention relates to isolated nucleic acid fragments encoding all or a substantial portion of *Vernonia galamenensis* fatty acid modifying enzymes. The invention also relates to the construction of chimeric genes encoding all or a portion of *Vernonia galamenensis* fatty acid modifying enzymes, in sense or antisense orientation, wherein expression of the chimeric gene results in production of altered levels of a *Vernonia galamenensis* fatty acid modifying enzymes in a transformed host cells.

17 Claims, 1 Drawing Sheet

FIG. 1

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1476 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
  ( A ) NAME/KEY: CDS
  ( B ) LOCATION: 134..1279

( x i ) SEQUENCE DESCRIPTION: SEQ ID NO:1:

```
GGCACGAGCT TCGCAGGCAC AGAGAAGGAA ATTGAGCGAT TAATCGCTTC TCCGAAGTGG        60

TTGTTTCTCC AGTGCAAACC CTAGGACTCC GTATATCGAT CGAATTAGGT TGAAGTGTCT       120

CCAGAACAAC AAA ATG GGA GCA GGA GGG TGC ATG TCT GCC TCC GAG ACA         169
            Met Gly Ala Gly Gly Cys Met Ser Ala Ser Glu Thr
             1               5                        10

AAA ACA CAA CAA AAG AAC CCT ATC GAG CGA GTC CCT TAT GCA AAA CCT         217
Lys Thr Gln Gln Lys Asn Pro Ile Glu Arg Val Pro Tyr Ala Lys Pro
         15                  20                  25

CCT TTC ACC ATC AGC GAC CTC AAA AAA GCC ATT CCT CCC CAC TGT TTC         265
Pro Phe Thr Ile Ser Asp Leu Lys Lys Ala Ile Pro Pro His Cys Phe
     30                  35                  40

CAG CGT TCC CTT ATC CGT TCC TTC TCT TAT GTC GTT TAT GAC CTT GCT         313
Gln Arg Ser Leu Ile Arg Ser Phe Ser Tyr Val Val Tyr Asp Leu Ala
 45                  50                  55                  60

GTG AGC TTC CTC CTC TAC TAT GTA GCC GCC ACT TAC TTC CAC CAT CTG         361
Val Ser Phe Leu Leu Tyr Tyr Val Ala Ala Thr Tyr Phe His His Leu
                 65                  70                  75

CCA AAC CCT TTC TCC TCC CTT GCG TGG CTG GCT TAT TGG GTC GTT CAA         409
Pro Asn Pro Phe Ser Ser Leu Ala Trp Leu Ala Tyr Trp Val Val Gln
             80                  85                  90

GGC TGT GTG CTT ACA GGA GTG TGG GTC ATA GCC CAT GAA TGT GGT CAC         457
Gly Cys Val Leu Thr Gly Val Trp Val Ile Ala His Glu Cys Gly His
         95                  100                 105

CAT GCA TTT AGT GAC TAT CAA TGG GTT GAT GAC ACT GTG GGC TTC CTA         505
His Ala Phe Ser Asp Tyr Gln Trp Val Asp Asp Thr Val Gly Phe Leu
     110                 115                 120

CTC CAC TCG GTT CTA CTT GTT CCT TTC TTT TCA TGG AAA TAC AGT CAT         553
Leu His Ser Val Leu Leu Val Pro Phe Phe Ser Trp Lys Tyr Ser His
125                 130                 135                 140

CGT CGA CAC CAC TCC AAC ACC GGA TCA CTC GAG CGT GAT GAA GTC TTT         601
Arg Arg His His Ser Asn Thr Gly Ser Leu Glu Arg Asp Glu Val Phe
                 145                 150                 155

GTC CCA AAA CCG AGA TCG AAA ATC CCT TGG TAC TCA AAA TAC TTT AAC         649
Val Pro Lys Pro Arg Ser Lys Ile Pro Trp Tyr Ser Lys Tyr Phe Asn
             160                 165                 170

AAC GCA CCT GGC CGC ATG ATG AGT GTG TTC ACC ACC CTA ACT CTA GGC         697
Asn Ala Pro Gly Arg Met Met Ser Val Phe Thr Thr Leu Thr Leu Gly
         175                 180                 185

TGG CCC TTG TAC TTG GTT TTC AAT GTA TCA GGG AGA CCC TAT GAC CGT         745
Trp Pro Leu Tyr Leu Val Phe Asn Val Ser Gly Arg Pro Tyr Asp Arg
     190                 195                 200

TTT GCC TGC CAC TTT TCT CCT AAC AGC CCT ATA TAC AAC GAA CGT GAG         793
Phe Ala Cys His Phe Ser Pro Asn Ser Pro Ile Tyr Asn Glu Arg Glu
205                 210                 215                 220

CGT CTC CAA ATA TGG CTT TCG GAT TTA GGG ATG ATC ACC ATG TCG TTC         841
Arg Leu Gln Ile Trp Leu Ser Asp Leu Gly Met Ile Thr Met Ser Phe
                 225                 230                 235

ATC CTT TAT CGT GTT GCT GTA GCA AAA GGT GTG GCT TGG GTA ATA TGC         889
Ile Leu Tyr Arg Val Ala Val Ala Lys Gly Val Ala Trp Val Ile Cys
             240                 245                 250

ATG TAT GGG ATC CCG CTA CTG ATT GTG AAC GGA TTC CTG GTG ACG ATC         937
Met Tyr Gly Ile Pro Leu Leu Ile Val Asn Gly Phe Leu Val Thr Ile
         255                 260                 265

ACG TAC CTT CAA CAC ACT CAC CCT TCA TTG CCC CAC TAT GAT AGC TCA         985
Thr Tyr Leu Gln His Thr His Pro Ser Leu Pro His Tyr Asp Ser Ser
```

```
                   270                        275                        280
GAG  TGG  GAC  TGG  CTA  AGG  GGA  GCA  ATG  GCA  ACG  GTG  GAC  CGT  GAC  TAT    1033
Glu  Trp  Asp  Trp  Leu  Arg  Gly  Ala  Met  Ala  Thr  Val  Asp  Arg  Asp  Tyr
285                      290                      295                      300

GGT  GTG  CTC  AAC  AAG  GTA  TTC  CAT  AAC  ATC  ACA  GAT  ACA  CAC  GTG  GTG    1081
Gly  Val  Leu  Asn  Lys  Val  Phe  His  Asn  Ile  Thr  Asp  Thr  His  Val  Val
                    305                      310                      315

CAC  CAT  TTG  TTC  TCG  ACG  ATG  CCT  CAT  TAT  AAC  GCA  ATG  GAG  GCA  ACG    1129
His  His  Leu  Phe  Ser  Thr  Met  Pro  His  Tyr  Asn  Ala  Met  Glu  Ala  Thr
               320                      325                      330

AAA  GCA  GTG  AAG  CCT  TTG  CTT  GGG  GAG  TAT  TAT  CAG  TTT  GAC  GGG  ACT    1177
Lys  Ala  Val  Lys  Pro  Leu  Leu  Gly  Glu  Tyr  Tyr  Gln  Phe  Asp  Gly  Thr
          335                      340                      345

CCG  TTT  TAC  GTA  GCA  ATA  TGG  AGA  GAG  GCA  AAG  GAG  TGT  CTG  TTC  GTG    1225
Pro  Phe  Tyr  Val  Ala  Ile  Trp  Arg  Glu  Ala  Lys  Glu  Cys  Leu  Phe  Val
350                      355                      360

GAT  CCA  GAT  GAG  GGG  GAG  GGT  CAG  GGA  GGT  GTG  TTT  TGG  TAC  AAG  AAT    1273
Asp  Pro  Asp  Glu  Gly  Glu  Gly  Gln  Gly  Gly  Val  Phe  Trp  Tyr  Lys  Asn
365                      370                      375                      380

AAG  ATG  TGATATTCAT  ATGATGAACA  AGTTTTATAG  GTTATCGATC  AGATCAGGTC             1329
Lys  Met

GGTTTATGTT  GTTTATGTGC  TTATGTGTGT  GTGTGTTTTT  TATGTGTAGC  AAGCAGTTGA            1389

TCGAGTGTTG  GGTATGTATG  TGTCGTAGCG  TCAATGAATT  GAAAAGAACT  GGTTATGTTC            1449

TTTAACATCA  AAAAAAAAAA  AAAAAA                                                   1476
```

( 2 ) INFORMATION FOR SEQ ID NO:2:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Ala  Gly  Gly  Cys  Met  Ser  Ala  Ser  Glu  Thr  Lys  Thr  Gln  Gln
 1                    5                      10                      15

Lys  Asn  Pro  Ile  Glu  Arg  Val  Pro  Tyr  Ala  Lys  Pro  Pro  Phe  Thr  Ile
                20                      25                      30

Ser  Asp  Leu  Lys  Lys  Ala  Ile  Pro  Pro  His  Cys  Phe  Gln  Arg  Ser  Leu
          35                      40                      45

Ile  Arg  Ser  Phe  Ser  Tyr  Val  Val  Tyr  Asp  Leu  Ala  Val  Ser  Phe  Leu
     50                      55                      60

Leu  Tyr  Tyr  Val  Ala  Ala  Thr  Tyr  Phe  His  His  Leu  Pro  Asn  Pro  Phe
65                      70                      75                      80

Ser  Ser  Leu  Ala  Trp  Leu  Ala  Tyr  Trp  Val  Val  Gln  Gly  Cys  Val  Leu
                    85                      90                      95

Thr  Gly  Val  Trp  Val  Ile  Ala  His  Glu  Cys  Gly  His  His  Ala  Phe  Ser
               100                     105                     110

Asp  Tyr  Gln  Trp  Val  Asp  Asp  Thr  Val  Gly  Phe  Leu  Leu  His  Ser  Val
          115                     120                     125

Leu  Leu  Val  Pro  Phe  Phe  Ser  Trp  Lys  Tyr  Ser  His  Arg  Arg  His  His
     130                     135                     140

Ser  Asn  Thr  Gly  Ser  Leu  Glu  Arg  Asp  Glu  Val  Phe  Val  Pro  Lys  Pro
145                     150                     155                     160

Arg  Ser  Lys  Ile  Pro  Trp  Tyr  Ser  Lys  Tyr  Phe  Asn  Asn  Ala  Pro  Gly
                    165                     170                     175
```

```
Arg  Met  Met  Ser  Val  Phe  Thr  Thr  Leu  Thr  Leu  Gly  Trp  Pro  Leu  Tyr
          180                      185                      190

Leu  Val  Phe  Asn  Val  Ser  Gly  Arg  Pro  Tyr  Asp  Arg  Phe  Ala  Cys  His
          195                      200                      205

Phe  Ser  Pro  Asn  Ser  Pro  Ile  Tyr  Asn  Glu  Arg  Glu  Arg  Leu  Gln  Ile
     210                      215                      220

Trp  Leu  Ser  Asp  Leu  Gly  Met  Ile  Thr  Met  Ser  Phe  Ile  Leu  Tyr  Arg
225                           230                 235                      240

Val  Ala  Val  Ala  Lys  Gly  Val  Ala  Trp  Val  Ile  Cys  Met  Tyr  Gly  Ile
               245                      250                      255

Pro  Leu  Leu  Ile  Val  Asn  Gly  Phe  Leu  Val  Thr  Ile  Thr  Tyr  Leu  Gln
               260                 265                      270

His  Thr  His  Pro  Ser  Leu  Pro  His  Tyr  Asp  Ser  Ser  Glu  Trp  Asp  Trp
          275                      280                      285

Leu  Arg  Gly  Ala  Met  Ala  Thr  Val  Asp  Arg  Asp  Tyr  Gly  Val  Leu  Asn
     290                      295                      300

Lys  Val  Phe  His  Asn  Ile  Thr  Asp  Thr  His  Val  Val  His  His  Leu  Phe
305                           310                 315                      320

Ser  Thr  Met  Pro  His  Tyr  Asn  Ala  Met  Glu  Ala  Thr  Lys  Ala  Val  Lys
                    325                 330                      335

Pro  Leu  Leu  Gly  Glu  Tyr  Tyr  Gln  Phe  Asp  Gly  Thr  Pro  Phe  Tyr  Val
               340                 345                      350

Ala  Ile  Trp  Arg  Glu  Ala  Lys  Glu  Cys  Leu  Phe  Val  Asp  Pro  Asp  Glu
               355                 360                      365

Gly  Glu  Gly  Gln  Gly  Gly  Val  Phe  Trp  Tyr  Lys  Asn  Lys  Met
               370                 375                 380
```

( 2 ) INFORMATION FOR SEQ ID NO:3:

( i ) SEQUENCE CHARACTERISTICS:
        ( A ) LENGTH: 1364 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 103..1254

( x i ) SEQUENCE DESCRIPTION: SEQ ID NO:3:

```
TTATGAAAGC  TCGATCGGTG  TTCGATCAAT  TCAAATCGAC  GAACACGAAA  TCGAACTCAA        60

CAATTCAAAT  CTGGAAATAT  TAATTGGATC  AAGCGGGCGG  AT  ATG  ATG  ATG  TCG       114
                                                    Met  Met  Met  Ser
                                                     1

GAT  TCA  TGT  GAT  GAT  CAT  GAT  CAG  CTG  GTG  AAA  GAT  GAT  CAT  AAT  ATA    162
Asp  Ser  Cys  Asp  Asp  His  Asp  Gln  Leu  Val  Lys  Asp  Asp  His  Asn  Ile
 5                        10                       15                       20

AAC  GAA  CGT  GCA  CCG  GTT  GAT  GCG  GCA  CCA  TTC  TCG  TTA  AGC  GAT  CTA    210
Asn  Glu  Arg  Ala  Pro  Val  Asp  Ala  Ala  Pro  Phe  Ser  Leu  Ser  Asp  Leu
                    25                       30                       35

AAG  AAA  GCA  ATC  CCT  CCG  CAT  TGC  TTC  CAG  CGA  TCT  GCC  ATC  CGT  TCA    258
Lys  Lys  Ala  Ile  Pro  Pro  His  Cys  Phe  Gln  Arg  Ser  Ala  Ile  Arg  Ser
               40                       45                       50

TCG  TGC  TAC  GTT  GTT  CAG  GAT  CTC  ATT  ATT  ACC  TTC  CTT  TTA  TAC  ACG    306
Ser  Cys  Tyr  Val  Val  Gln  Asp  Leu  Ile  Ile  Thr  Phe  Leu  Leu  Tyr  Thr
          55                       60                       65

CTC  GCC  AAC  TCT  TAC  ATT  CCT  CTT  CTT  CCT  CCT  CCT  CTA  CCT  TAC  TTA    354
Leu  Ala  Asn  Ser  Tyr  Ile  Pro  Leu  Leu  Pro  Pro  Pro  Leu  Pro  Tyr  Leu
```

-continued

```
               70                           75                           80
GCA  TGG  CCT  GTT  TAC  TGG  TTT  TGC  CAA  TCT  TCG  ATC  CTC  ACT  GGT  TTA        402
Ala  Trp  Pro  Val  Tyr  Trp  Phe  Cys  Gln  Ser  Ser  Ile  Leu  Thr  Gly  Leu
 85                 90                      95                          100

TGG  GTC  ATT  GGC  CAT  GAA  TGT  GGC  CAT  CAT  GCT  TAT  AGT  GAG  TAC  CAG        450
Trp  Val  Ile  Gly  His  Glu  Cys  Gly  His  His  Ala  Tyr  Ser  Glu  Tyr  Gln
                    105                      110                      115

TGG  GTT  GAT  AAC  ACC  GTT  GGA  TTC  ATC  CTC  CAT  TCC  TTT  CTT  CTC  ACA        498
Trp  Val  Asp  Asn  Thr  Val  Gly  Phe  Ile  Leu  His  Ser  Phe  Leu  Leu  Thr
                    120                      125                      130

CCT  TAC  TTT  TCT  TGG  AAA  TAC  AGC  CAT  CGA  AAG  CAC  CAT  GCC  AAC  ACG        546
Pro  Tyr  Phe  Ser  Trp  Lys  Tyr  Ser  His  Arg  Lys  His  His  Ala  Asn  Thr
          135                      140                      145

AAT  TCA  CTC  GAA  AAC  GAG  GAG  GTT  TAC  ATT  CCT  AAA  GCC  AAG  TCC  CAG        594
Asn  Ser  Leu  Glu  Asn  Glu  Glu  Val  Tyr  Ile  Pro  Lys  Ala  Lys  Ser  Gln
     150                      155                      160

CTC  AGG  AAT  TAC  TCC  AAT  TTC  AAA  TTT  CTT  GAC  AAC  ACC  CCT  GGT  CGA        642
Leu  Arg  Asn  Tyr  Ser  Asn  Phe  Lys  Phe  Leu  Asp  Asn  Thr  Pro  Gly  Arg
165                      170                      175                      180

ATC  TTC  ATT  TTG  CTT  ATC  ATG  TTG  ACC  TTG  GGC  TTT  CCT  TTA  TAC  CTC        690
Ile  Phe  Ile  Leu  Leu  Ile  Met  Leu  Thr  Leu  Gly  Phe  Pro  Leu  Tyr  Leu
                         185                      190                      195

TTG  ACC  AAT  ATT  TCA  GGC  AAG  AAA  TAC  CAA  AGG  TTT  GCC  AAC  CAC  TTT        738
Leu  Thr  Asn  Ile  Ser  Gly  Lys  Lys  Tyr  Gln  Arg  Phe  Ala  Asn  His  Phe
                    200                      205                      210

GAT  CCG  TTG  AGC  CCC  ATC  TTC  AGT  GAG  CGT  GAA  CGA  ATC  CAG  GTC  GTG        786
Asp  Pro  Leu  Ser  Pro  Ile  Phe  Ser  Glu  Arg  Glu  Arg  Ile  Gln  Val  Val
               215                      220                      225

CTA  TCG  GAT  GTG  GGT  CTC  ATT  GCT  GTG  TTT  TAC  GGG  CTT  AAG  TTT  CTT        834
Leu  Ser  Asp  Val  Gly  Leu  Ile  Ala  Val  Phe  Tyr  Gly  Leu  Lys  Phe  Leu
     230                      235                      240

GTA  GCG  AAA  AAA  GGG  TTC  GGT  TGG  GTA  ATG  CGC  ATG  TAC  GGA  GCC  CCA        882
Val  Ala  Lys  Lys  Gly  Phe  Gly  Trp  Val  Met  Arg  Met  Tyr  Gly  Ala  Pro
245                      250                      255                      260

GTG  GTT  GGG  CTG  AAT  GCC  TTC  ATA  ATA  ATG  ATC  ACT  TAT  CTC  CAC  CAC        930
Val  Val  Gly  Leu  Asn  Ala  Phe  Ile  Ile  Met  Ile  Thr  Tyr  Leu  His  His
                         265                      270                      275

ACC  CAT  CTG  TCT  TCG  CCT  CAT  TAC  GAT  TCG  ACC  GAA  TGG  AAC  TGG  ATC        978
Thr  His  Leu  Ser  Ser  Pro  His  Tyr  Asp  Ser  Thr  Glu  Trp  Asn  Trp  Ile
                    280                      285                      290

AAA  GGA  GCC  TTG  ACT  ACA  ATC  GAT  AGA  GAT  TTC  GGT  CTC  CTG  AAT  AGG       1026
Lys  Gly  Ala  Leu  Thr  Thr  Ile  Asp  Arg  Asp  Phe  Gly  Leu  Leu  Asn  Arg
               295                      300                      305

GTG  TTC  CAT  GAC  GTC  ACT  CAC  ACA  CAC  GTG  TTG  CAT  CAT  TTG  TTC  CCG       1074
Val  Phe  His  Asp  Val  Thr  His  Thr  His  Val  Leu  His  His  Leu  Phe  Pro
     310                      315                      320

TAC  ATT  CCA  CAT  TAT  CAT  GCA  AAG  GAG  GCG  AGC  GAC  GCA  ATA  AAG  CCG       1122
Tyr  Ile  Pro  His  Tyr  His  Ala  Lys  Glu  Ala  Ser  Asp  Ala  Ile  Lys  Pro
325                      330                      335                      340

GTG  TTA  GGG  GAG  TAT  CGG  ATG  ATC  GAT  AGG  ACT  CCG  TTT  TAC  AAA  GCA       1170
Val  Leu  Gly  Glu  Tyr  Arg  Met  Ile  Asp  Arg  Thr  Pro  Phe  Tyr  Lys  Ala
                    345                      350                      355

ATG  TGG  AGA  GAG  GCG  AAG  GAA  TGC  ATC  TAC  ATC  GAG  CCA  GAT  GAA  GAT       1218
Met  Trp  Arg  Glu  Ala  Lys  Glu  Cys  Ile  Tyr  Ile  Glu  Pro  Asp  Glu  Asp
               360                      365                      370

AAG  AAG  CAC  AAA  GGT  GTA  TAT  TGG  TAC  CAT  AAA  ATG  TGATACGAGC                1264
Lys  Lys  His  Lys  Gly  Val  Tyr  Trp  Tyr  His  Lys  Met
          375                      380

TGAGTACGTA  GTACGTTGTA  TGCTTTTGTA  ACGTTTTGTA  AGATAAATAA  ATAAATCTTG               1324
```

AATGAAGATA AAAAAAAAA AAAAAAAAA AAAAAAAAA                                                                    1364

(2) INFORMATION FOR SEQ ID NO:4:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:4:

```
Met Met Met Ser Asp Ser Cys Asp Asp His Asp Gln Leu Val Lys Asp
 1               5                  10                  15
Asp His Asn Ile Asn Glu Arg Ala Pro Val Asp Ala Ala Pro Phe Ser
             20                  25                  30
Leu Ser Asp Leu Lys Lys Ala Ile Pro Pro His Cys Phe Gln Arg Ser
         35                  40                  45
Ala Ile Arg Ser Ser Cys Tyr Val Val Gln Asp Leu Ile Ile Thr Phe
     50                  55                  60
Leu Leu Tyr Thr Leu Ala Asn Ser Tyr Ile Pro Leu Leu Pro Pro Pro
 65                  70                  75                  80
Leu Pro Tyr Leu Ala Trp Pro Val Tyr Trp Phe Cys Gln Ser Ser Ile
             85                  90                  95
Leu Thr Gly Leu Trp Val Ile Gly His Glu Cys Gly His His Ala Tyr
            100                 105                 110
Ser Glu Tyr Gln Trp Val Asp Asn Thr Val Gly Phe Ile Leu His Ser
            115                 120                 125
Phe Leu Leu Thr Pro Tyr Phe Ser Trp Lys Tyr Ser His Arg Lys His
    130                 135                 140
His Ala Asn Thr Asn Ser Leu Glu Asn Glu Glu Val Tyr Ile Pro Lys
145                 150                 155                 160
Ala Lys Ser Gln Leu Arg Asn Tyr Ser Asn Phe Lys Phe Leu Asp Asn
                165                 170                 175
Thr Pro Gly Arg Ile Phe Ile Leu Leu Ile Met Leu Thr Leu Gly Phe
            180                 185                 190
Pro Leu Tyr Leu Leu Thr Asn Ile Ser Gly Lys Lys Tyr Gln Arg Phe
        195                 200                 205
Ala Asn His Phe Asp Pro Leu Ser Pro Ile Phe Ser Glu Arg Glu Arg
210                 215                 220
Ile Gln Val Val Leu Ser Asp Val Gly Leu Ile Ala Val Phe Tyr Gly
225                 230                 235                 240
Leu Lys Phe Leu Val Ala Lys Lys Gly Phe Gly Trp Val Met Arg Met
                245                 250                 255
Tyr Gly Ala Pro Val Val Gly Leu Asn Ala Phe Ile Ile Met Ile Thr
            260                 265                 270
Tyr Leu His His Thr His Leu Ser Ser Pro His Tyr Asp Ser Thr Glu
        275                 280                 285
Trp Asn Trp Ile Lys Gly Ala Leu Thr Thr Ile Asp Arg Asp Phe Gly
    290                 295                 300
Leu Leu Asn Arg Val Phe His Asp Val Thr His Thr His Val Leu His
305                 310                 315                 320
His Leu Phe Pro Tyr Ile Pro His Tyr His Ala Lys Glu Ala Ser Asp
                325                 330                 335
Ala Ile Lys Pro Val Leu Gly Glu Tyr Arg Met Ile Asp Arg Thr Pro
            340                 345                 350
```

```
Phe  Tyr  Lys  Ala  Met  Trp  Arg  Glu  Ala  Lys  Glu  Cys  Ile  Tyr  Ile  Glu
          355                      360                      365

Pro  Asp  Glu  Asp  Lys  Lys  His  Lys  Gly  Val  Tyr  Trp  Tyr  His  Lys  Met
          370                      375                      380
```

( 2 ) INFORMATION FOR SEQ ID NO:5:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Gly  Leu  Ala  Lys  Glu  Thr  Thr  Met  Gly  Gly  Arg  Gly  Arg  Val  Ala
 1                       5                       10                       15

Lys  Val  Glu  Val  Gln  Gly  Lys  Lys  Pro  Leu  Ser  Arg  Val  Pro  Asn  Thr
          20                      25                       30

Lys  Pro  Pro  Phe  Thr  Val  Gly  Gln  Leu  Lys  Lys  Ala  Ile  Pro  Pro  His
          35                      40                       45

Cys  Phe  Gln  Arg  Ser  Leu  Leu  Thr  Ser  Phe  Ser  Tyr  Val  Val  Tyr  Asp
     50                       55                       60

Leu  Ser  Phe  Ala  Phe  Ile  Phe  Tyr  Ile  Ala  Thr  Thr  Tyr  Phe  His  Leu
 65                      70                       75                       80

Leu  Pro  Gln  Pro  Phe  Ser  Leu  Ile  Ala  Trp  Pro  Ile  Tyr  Trp  Val  Leu
               85                       90                       95

Gln  Gly  Cys  Leu  Leu  Thr  Gly  Val  Trp  Val  Ile  Ala  His  Glu  Cys  Gly
               100                      105                      110

His  His  Ala  Phe  Ser  Lys  Tyr  Gln  Trp  Val  Asp  Asp  Val  Val  Gly  Leu
          115                      120                      125

Thr  Leu  His  Ser  Thr  Leu  Leu  Val  Pro  Tyr  Phe  Ser  Trp  Lys  Ile  Ser
     130                      135                      140

His  Arg  Arg  His  His  Ser  Asn  Thr  Gly  Ser  Leu  Asp  Arg  Asp  Glu  Val
145                      150                      155                      160

Phe  Val  Pro  Lys  Pro  Lys  Ser  Lys  Val  Ala  Trp  Phe  Ser  Lys  Tyr  Leu
               165                      170                      175

Asn  Asn  Pro  Leu  Gly  Arg  Ala  Val  Ser  Leu  Leu  Val  Thr  Leu  Thr  Ile
               180                      185                      190

Gly  Trp  Pro  Met  Tyr  Leu  Ala  Phe  Asn  Val  Ser  Gly  Arg  Pro  Tyr  Asp
          195                      200                      205

Ser  Phe  Ala  Ser  His  Tyr  His  Pro  Tyr  Ala  Pro  Ile  Tyr  Ser  Asn  Arg
     210                      215                      220

Glu  Arg  Leu  Leu  Ile  Tyr  Val  Ser  Asp  Val  Ala  Leu  Phe  Ser  Val  Thr
225                      230                      235                      240

Tyr  Ser  Leu  Tyr  Arg  Val  Ala  Thr  Leu  Lys  Gly  Leu  Val  Trp  Leu  Leu
               245                      250                      255

Cys  Val  Tyr  Gly  Val  Pro  Leu  Leu  Ile  Val  Asn  Gly  Phe  Leu  Val  Thr
               260                      265                      270

Ile  Thr  Tyr  Leu  Gln  His  Thr  His  Phe  Ala  Leu  Pro  His  Tyr  Asp  Ser
          275                      280                      285

Ser  Glu  Trp  Asp  Trp  Leu  Lys  Gly  Ala  Leu  Ala  Thr  Met  Asp  Arg  Asp
     290                      295                      300

Tyr  Gly  Ile  Leu  Asn  Lys  Val  Phe  His  His  Ile  Thr  Asp  Thr  His  Val
305                      310                      315                      320

Ala  His  His  Leu  Phe  Ser  Thr  Met  Pro  His  Tyr  His  Ala  Met  Glu  Ala
               325                      330                      335
```

```
Thr  Asn  Ala  Ile  Lys  Pro  Ile  Leu  Gly  Glu  Tyr  Tyr  Gln  Phe  Asp  Asp
               340                      345                     350

Thr  Pro  Phe  Tyr  Lys  Ala  Leu  Trp  Arg  Glu  Ala  Arg  Glu  Cys  Leu  Tyr
               355                      360                     365

Val  Glu  Pro  Asp  Glu  Gly  Thr  Ser  Glu  Lys  Gly  Val  Tyr  Trp  Tyr  Arg
     370                      375                     380

Asn  Lys  Tyr
385
```

(2) INFORMATION FOR SEQ ID NO:6:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Gly  Gly  Gly  Gly  Arg  Met  Ser  Thr  Val  Ile  Thr  Ser  Asn  Asn  Ser
 1                        5                    10                      15

Glu  Lys  Lys  Gly  Gly  Ser  Ser  His  Leu  Lys  Arg  Ala  Pro  His  Thr  Lys
               20                      25                      30

Pro  Pro  Phe  Thr  Leu  Gly  Asp  Leu  Lys  Arg  Ala  Ile  Pro  Pro  His  Cys
               35                      40                      45

Phe  Glu  Arg  Ser  Phe  Val  Arg  Ser  Phe  Ser  Tyr  Val  Ala  Tyr  Asp  Val
     50                      55                      60

Cys  Leu  Ser  Phe  Leu  Phe  Tyr  Ser  Ile  Ala  Thr  Asn  Phe  Phe  Pro  Tyr
 65                      70                      75                       80

Ile  Ser  Ser  Pro  Leu  Ser  Tyr  Val  Ala  Trp  Leu  Val  Tyr  Trp  Leu  Phe
               85                      90                          95

Gln  Gly  Cys  Ile  Leu  Thr  Gly  Leu  Trp  Val  Ile  Gly  His  Glu  Cys  Gly
               100                     105                     110

His  His  Ala  Phe  Ser  Glu  Tyr  Gln  Leu  Ala  Asp  Asp  Ile  Val  Gly  Leu
          115                     120                     125

Ile  Val  His  Ser  Ala  Leu  Leu  Val  Pro  Tyr  Phe  Ser  Trp  Lys  Tyr  Ser
     130                     135                     140

His  Arg  Arg  His  His  Ser  Asn  Ile  Gly  Ser  Leu  Glu  Arg  Asp  Glu  Val
145                      150                     155                     160

Phe  Val  Pro  Lys  Ser  Lys  Ser  Lys  Ile  Ser  Trp  Tyr  Ser  Lys  Tyr  Ser
               165                     170                     175

Asn  Asn  Pro  Pro  Gly  Arg  Val  Leu  Thr  Leu  Ala  Ala  Thr  Leu  Leu  Leu
               180                     185                     190

Gly  Trp  Pro  Leu  Tyr  Leu  Ala  Phe  Asn  Val  Ser  Gly  Arg  Pro  Tyr  Asp
          195                     200                     205

Arg  Phe  Ala  Cys  His  Tyr  Asp  Pro  Tyr  Gly  Pro  Ile  Phe  Ser  Glu  Arg
     210                     215                     220

Glu  Arg  Leu  Gln  Ile  Tyr  Ile  Ala  Asp  Leu  Gly  Ile  Phe  Ala  Thr  Thr
225                      230                     235                     240

Phe  Val  Leu  Tyr  Gln  Ala  Thr  Met  Ala  Lys  Gly  Leu  Ala  Trp  Val  Met
               245                     250                     255

Arg  Ile  Tyr  Gly  Val  Pro  Leu  Leu  Ile  Val  Asn  Cys  Phe  Leu  Val  Met
               260                     265                     270

Ile  Thr  Tyr  Leu  Gln  His  Thr  His  Pro  Ala  Ile  Pro  Arg  Tyr  Gly  Ser
               275                     280                     285

Ser  Glu  Trp  Asp  Trp  Leu  Arg  Gly  Ala  Met  Val  Thr  Val  Asp  Arg  Asp
```

```
                        290                           295                            300
Tyr  Gly  Val  Leu  Asn  Lys  Val  Phe  His  Asn  Ile  Ala  Asp  Thr  His  Val
305                      310                      315                           320

Ala  His  His  Leu  Phe  Ala  Thr  Val  Pro  His  Tyr  His  Ala  Met  Glu  Ala
                    325                      330                     335

Thr  Lys  Ala  Ile  Lys  Pro  Ile  Met  Gly  Glu  Tyr  Tyr  Arg  Tyr  Asp  Gly
                    340                      345                     350

Thr  Pro  Phe  Tyr  Lys  Ala  Leu  Trp  Arg  Glu  Ala  Lys  Glu  Cys  Leu  Phe
               355                      360                     365

Val  Glu  Pro  Asp  Glu  Gly  Ala  Pro  Thr  Gln  Gly  Val  Phe  Trp  Tyr  Arg
          370                      375                     380

Asn  Lys  Tyr
385
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

ATGCGGCCGC ATGATGATGT CGGATTCATG     30

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

ATGCGGCCGC TCACATTTTA TGGTACCAAT AT     32

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

ATGCGGCCGC CATGGGAGCA GGAGGG     26

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

ATGCGGCCGC TCACATCTTA TTCTTGTACC AA     32

FATTY ACID MODIFYING ENZYMES FROM DEVELOPING SEEDS OF *VERNONIA GALAMENENSIS*

FIELD OF THE INVENTION

This invention is in the field of plant molecular biology. More specifically, this invention pertains to nucleic acid fragments encoding enzymes involved in fatty acid biosynthesis and modification in plants and seeds.

BACKGROUND OF THE INVENTION

Fatty acids bearing chemical modifications in addition to the common double bonds are found in the storage lipids of many oilseeds (Harwood, J. L. (1980) In The Biochemistry of Plants, T. S. Moore Jr., ed. CRC Press, New York, pp 91–116). Some of these modifications functionalize the fatty acid to produce products that are useful in industrial applications; this is opposed to the more common usage of plant-derived lipids as foods. Examples are the use of the hydroxylated fatty acid ricinoleic acid in lubricants, and the short- or medium-carbon chain length fatty acids from palm oil in detergents. In some cases, fatty acid composition of the storage lipids of oilseeds produced in temperate climates can be modified by the addition of genes from exotic sources so that large amounts of unique fatty acids are produced (Ohlrogge, J B. (1994) *Plant Physiol.* 104, 821–826).

Epoxidation is among the known modifications to storage lipid fatty acids. The 18-carbon fatty acid 9,10-ene-12,13-epoxide comprises as much as 60% of the total seed fatty acid in species such as *Vernonia galamenensis* and *Euphorbia lagascea* (Bafor, M. et al. (1993) *Arch. Biochem Biophys* 303:145–151). Fatty acids carrying the epoxide modification may find use as plasticizers, in crosslinking coatings applications, and in setting printing inks.

Attempts to delineate the biosynthetic pathway of cis-12-epoxyoctadeca-cis-9-enoate indicate that the catalytic activity responsible for the introduction of the epoxide moiety is in the microsomal membrane fraction, most likely the endoplasmic reticulum (Bafor et al. supra). While the above study also suggests that the catalytic activity responsible is an enzyme in the cytochrome P450 mono-oxygenase class, enzymes with amino acid sequences related to the endoplasmic reticulum-localized fatty acid desaturases have been isolated from tissues that produce hydroxylated fatty acids (World Patent Publication No. WO94/11516). These sequences have been shown to be active in adding the hydroxyl group to esterified fatty acids (Broun, P. and Somerville, C. (1997) *Plant Physiol* 113: 933–942). It is therefore possible that fatty acid epoxidizing enzymes may be related in sequence to the class of membrane bound enzymes responsible for fatty acid desaturation and fatty acid hydroxylation.

Thus while candidate enzyme classes have been suggested, no gene sequences from those candidate classes and from tissues that are known to produce epoxidized fatty acids have been isolated.

SUMMARY OF THE INVENTION

The instant invention relates to isolated nucleic acid fragments encoding plant enzymes involved in fatty acid biosynthesis and modification, the enzymes having sequence homology to membrane-bound fatty acid desaturases. Specifically, this invention concerns isolated nucleic acid fragments encoding a fatty acid epoxidizing enzyme and a fatty acid desaturase enzyme, each of which are normally expressed in developing seeds of *Vernonia galamenensis*. In addition, this invention relates to nucleic acid fragments that are complementary to nucleic acid fragments encoding the *Vernonia galamenensis* fatty acid epoxidizing and desaturase enzymes.

In another embodiment, the instant invention relates chimeric genes that comprise nucleic acid fragments encoding *Vernonia galamenensis* fatty acid epoxidizing or desaturase enzymes operably linked to suitable regulatory sequences, wherein expression of the chimeric genes results in production of levels of the encoded protein in transformed host cells. For example, disclosed herein is a chimeric gene wherein a nucleic acid fragment encoding a *Vernonia galamenensis* fatty acid epoxidizing enzyme or a *Vernonia galamenensis* fatty acid desaturase enzyme is operably linked to one or more regulatory sequences suitable for directing expression of the *Vernonia galamenensis* fatty acid epoxidizing or desaturase enzymes in microbial cells.

In a further embodiment, the instant invention concerns a transformed host cell comprising in its genome a chimeric gene comprising a nucleic acid fragment encoding a *Vernonia galamenensis* fatty acid epoxidizing or desaturase enzyme operably linked to suitable regulatory sequences. Expression of the chimeric gene results in production of altered levels of protein encoded by the operably linked nucleic acid fragment in the transformed host cell. The transformed host cell can be of eukaryotic or prokaryotic origin, and include cells derived from higher plants and microorganisms. The invention also includes transformed plants that arise from transformed host cells of higher plants, and from seeds derived from such transformed plants.

An additional embodiment of the instant invention concerns a method of altering the level of expression of a *Vernonia galamenensis* fatty acid epoxidizing enzyme or a *Vernonia galamenensis* fatty acid desaturase enzyme in a transformed host cell comprising: a) transforming a host cell with a chimeric gene comprising a nucleic acid fragment encoding a *Vernonia galamenensis* fatty acid epoxidizing enzyme or a *Vernonia galamenensis* fatty acid desaturase enzyme; and b) growing the transformed host cell under conditions that are suitable for expression of the chimeric gene wherein expression of the chimeric gene results in production of altered levels of protein encoded by the operably linked nucleic acid fragment in the transformed host cell.

Yet another embodiment of the instant invention concerns a method for producing epoxidized fatty acids in the seeds of plants comprising the following steps: (a) transforming a plant cell with a chimeric gene encoding all or a portion of the *Vernonia galamenensis* fatty acid epoxidizing enzyme operably linked in sense orientation to suitable regulatory sequences; (b) growing a fertile mature plant from the transformed plant cell of step (a) under conditions suitable to obtain seeds; and (c) selecting from the progeny seed of step (b) those seeds containing epoxidized fatty acids.

Another embodiment of the instant invention is a method for producing *Vernonia galamenensis* fatty acid epoxidizing enzyme or *Vernonia galamenensis* fatty acid desaturase enzyme comprising the following steps: (a) transforming a microbial host cell with a chimeric gene wherein a nucleic acid fragment encoding a *Vernonia galamenensis* fatty acid epoxidizing enzyme or a *Vernonia galamenensis* fatty acid desaturase enzyme is operably linked to regulatory sequences suitable for directing expression in microbial cells; and (b) growing the transformed microbial cells obtained from step (a) under conditions that result in expression of the *Vernonia galamenensis* fatty acid epoxidizing or desaturase enzyme proteins.

An additional embodiment of the instant invention concerns a method for obtaining a nucleic acid fragment encoding all or substantially all of an amino acid sequence encoding *Vernonia galamenensis* fatty acid epoxidizing or desaturase enzymes.

BRIEF DESCRIPTION OF THE DRAWINGS AND SEQUENCE DESCRIPTIONS

The invention can be more fully understood from the following detailed description and the accompanying drawing and sequence descriptions which form a part of this application.

FIG. 1 shows a comparison of the amino acid sequences of the instant *Vernonia galamenensis* fatty acid desaturase (vs1.05h08), the instant *Vernonia galamenensis* fatty acid epoxidase (vs1.02c07), a soybean fatty acid desaturase (soy) and a castor bean fatty acid hydroxylase (castor). The eight conserved histidine residues found in all membrane bound fatty acid modifying enzymes of this class are boxed and stippled. An arginine residue found in the fatty acid hydroxylase from castor bean and in the instant *Vernonia galamenensis* fatty acid epoxidase but not in the fatty acid desaturating enzymes of this class is also boxed and stippled. Other residues in the Vernonia fatty acid epoxidase sequence that are unique to that sequence but conserved in most or all of the other sequences are boxed. Not all amino acid changes are marked: only those in which the change in the epoxidase sequence occurs in a highly conserved region and in which the amino acid present in the epoxidase is different in physical character from the conserved residues in the other sequences are marked.

The following sequence descriptions and sequence listings attached hereto comply with the rules governing nucleotide and/or amino acid sequence disclosures in patent applications as set forth in 37 C.F.R. §1.821–1.825.

SEQ ID NO:1 is the nucleotide sequence comprising the cDNA insert in clone vs1.05h08 encoding a *Vernonia galamenensis* fatty acid desaturase enzyme.

SEQ ID NO:2 is the deduced amino acid sequence of a *Vernonia galamenensis* fatty acid desaturase enzyme derived from the nucleotide sequence of SEQ ID NO: 1.

SEQ ID NO:3 is the nucleotide sequence comprising the cDNA insert in clone vs1.02c07 encoding a *Vernonia galamenensis* fatty acid epoxidizing enzyme.

SEQ ID NO:4 is the deduced amino acid sequence of a *Vernonia galamenensis* fatty acid epoxidizing enzyme derived from the nucleotide sequence of SEQ ID NO:3.

SEQ ID NO:5 is the amine acid sequence encoding the soybean (*Glycine max*) fatty acid desaturase enzyme depicted in FIG. 1 and having GenBank Accession No. L43920.

SEQ ID NO:6 is the amino acid sequence encoding the castor bean (*Ricinus communis*) fatty acid hydroxylase enzyme depicted in FIG. 1 and having GenBank Accession No. U22378.

SEQ ID NO:7 shows the nucleotide sequence of the PCR primer used as the 5' end primer in PCR reactions for amplification of the coding region of vs1.02c07.

SEQ ID NO:8 shows the nucleotide sequence of the PCR primer used as the 3' end primer in PCR reactions for amplification of the coding region of vs1.02c07.

SEQ ID NO:9 shows the nucleotide sequence of the PCR primer used as the 5' end primer in PCR reactions for amplification of the coding region of vs1.05h08.

SEQ ID NO: 10 shows the nucleotide sequence of the PCR primer used as the 3' end primer in PCR reactions for amplification of the coding region of vs1.05h08.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth 37 C.F.R. §1.822.

DETAILED DESCRIPTION OF THE INVENTION

This invention relates to isolated nucleic acid fragments encoding all or a substantial portion of fatty acid epoxidizing and desaturase enzymes normally expressed in developing seeds of *Vernonia galamenensis* that are similar in sequence to other plant, membrane-bound fatty acid desaturases. The invention also relates to the construction of a chimeric gene comprising an nucleic acid fragment encoding all or a portion of the *Vernonia galamenensis* fatty acid epoxidizing or desaturase enzyme, operably linked in sense or antisense orientation to suitable regulatory sequences, wherein expression of the chimeric gene results in production of altered levels of the desired enzyme in a transformed host cell. The invention also relates to methods of using isolated nucleic acid fragments encoding all or a substantial portion of the fatty acid epoxidizing and desaturase enzymes normally expressed in developing seeds of *Vernonia galamenensis*.

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "*Vernonia galamenensis* fatty acid modifying enzyme" refers collectively to the *Vernonia galamenensis* fatty acid epoxidizing enzyme and the *Vernonia galamenensis* fatty acid desaturase enzyme disclosed in the instant specification.

As used herein, "substantially similar" refers to nucleic acid fragments wherein changes in one or more nucleotides results in substitution of one or more amino acids, but do not affect the functional properties of the protein encoded by the DNA sequence. "Substantially similar" also refers to nucleic acid fragments wherein changes in one or more nucleotides does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403–410; see also www.ncbi.nlm.nih.gov/ BLAST/). In general, a sequence often or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of an amino acid or nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the *Vernonia galamenensis* fatty acid desaturase enzyme as set forth in SEQ ID NO:2, and to any nucleic acid fragment that encodes all or a substantial portion of the amino acid sequence encoding the *Vernonia galamenensis* fatty acid epoxidizing enzyme as set forth in SEQ ID NO:4. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding 5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences refer to DNA sequences" located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al , (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript; or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. The protein is to be directed to the nucleus, any signal peptide present should be removed and instead a nuclear localization signal included (Raikhel (1992) *Plant Phys.* 100: 1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

This invention relates to plant cDNAs with homology to fatty acid desaturase enzymes from other plant species. Several cDNA clones encoding *Vernonia galamenensis* fatty acid modifying enzymes have been isolated and identified by comparison of random plant cDNA sequences to the GenBank database using the BLAST algorithms well known to those skilled in the art. The nucleotide sequence encoding the *Vernonia galamenensis* fatty acid desaturase enzyme is provided in SEQ ID NO: 1, and the deduced amino acid sequence is provided in SEQ ID NO:2. The nucleotide sequence encoding the *Vernonia galamenensis* fatty acid epoxidizing enzyme is provided in SEQ ID NO:3, and the deduced amino acid sequence is provided in SEQ ID NO:4. Fatty acid desaturase and epoxidizing enzymes genes from other plants can now be identified by comparison of random cDNA sequences to the *Vernonia galamenensis* sequences provided herein.

The amino acid sequences encoded by the cDNA clones disclosed herein are compared in FIG. 1 to the fatty acid desaturase from soybean which inserts the second double bond between carbon atoms 12 and 13 into monounsaturated fatty acid, oleic acid, to produce linoleic acid. The sequence of a similar enzyme from castor bean which functions to hydroxylate the number 12 carbon atom of oleic acid to produce ricinoleic acid is also shown for comparison. While both *Vernonia galamenensis* sequences possess the highly conserved amino acid residues that are common to this class of enzyme, one of the clones, vs1.05h08, demonstrates greater similarity the soybean sequence than vs1.02c07. The amino acid sequence encoded by cDNA clone vs1.05h08 is 70.2% similar to the soybean sequence, while the sequence encoded by cDNA clone vs1.02c07 is only 53.8% similar. As well, the two *Vernonia galamenensis* sequences show only 57.7% similarity to each other as opposed to the much greater sequence similarity shown between species by vs1.05h08.

In *Vernonia galamenensis*, as with other species that produce unusual fatty acids, production of these unusual acids is limited to seed storage tissue. Moreover, the unusual fatty acids are generally not found in other parts of the plant. No signal was detected following Northern analysis of mRNA isolated from leaves of *Vernonia galamenensis* when vs1.02c07 was used as a probe, while the message was very abundant in mRNA isolated from developing seeds.

The sequence relationship of vs1.02c07 to other, known fatty acid desaturases, along with its tissue-specific expression pattern in a tissue that is actively producing the epoxidized fatty acid vernoleate, make it very likely that the enzyme encoded by cDNA clone vs1.02c07 is a fatty acid epoxidase. In contrast, sequence comparisons indicate that cDNA clone vs1.05h08 encodes a fatty acid desaturase enzyme.

The nucleic acid fragments of the instant invention may be used to isolate cDNAs and genes encoding homologous fatty acid modifying enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding homologous fatty acid modifying enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and uses as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS U.S.A.* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS U.S.A.* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the *Vernonia galamenensis* fatty acid modifying enzymes are present at higher levels than normal or in cell types or developmental stages in which it is not normally found. For example, when over-expressed in plant cells, the *Vernonia galamenensis* fatty acid epoxidizing enzyme may be useful for causing the biosynthesis and accumulation of epoxidized fatty acids in those cells. It is particularly useful to use the *Vernonia galamenensis* fatty acid epoxidizing enzyme gene to produce epoxidized fatty acids in the cells of the seeds of oilseed crop plants.

Overexpression of the *Vernonia galamenensis* fatty acid epoxidizing or desaturase enzymes may be accomplished by first constructing a chimeric gene in which the *Vernonia galamenensis* fatty acid epoxidizing or desaturase enzyme coding region is operably linked to a promoter capable of directing expression of a gene in the desired tissues at the desired stage of development. For reasons of convenience, the chimeric gene may comprise a promoter sequence and translation leader sequence derived from the same gene. 3' non-coding sequences encoding transcription termination signals may also be provided. The instant chimeric genes may also comprise one or more introns in order to facilitate gene expression.

Plasmid vectors comprising the instant chimeric genes can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant *Vernonia galamenensis* fatty acid modifying enzymes to different cellular compartments, or to facilitate its secretion from the cell. It is thus envisioned that the chimeric genes described above may be further supplemented by altering the coring sequences to encode *Vernonia galamenensis* fatty acid modifying enzymes disclosed herein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.*100:1627–1632) added and/or with targeting sequences that are already present removed. While the references cited give examples of each of these, the list is not exhaustive and more targeting signals of utility may be discovered in the future.

The instant *Vernonia galamenensis* fatty acid modifying enzymes (or portions of the enzymes) may be produced in heterologous host cells, particularly in the cells of microbial hosts, and can be used to prepare antibodies to the *Vernonia galamenensis* fatty acid epoxidizing and desaturase enzymes by methods well known to those skilled in the art. The antibodies are useful for detecting the instant *Vernonia galamenensis* fatty acid modifying enzymes in situ in cells or in vitro in cell extracts. Preferred heterologous host cells for production of the instant *Vernonia galamenensis* fatty acid modifying enzymes are microbial hosts. Microbial expression systems and expression vectors containing regulatory sequences that direct high level expression of foreign proteins are well known to those skilled in the art. Any of these could be used to construct chimeric genes for production of the instant *Vernonia galamenensis* fatty acid epoxidizing enzyme or the instant *Vernonia galamenensis* fatty acid desaturase enzyme. These chimeric genes could then be introduced into appropriate microorganisms via transformation to provide high level expression of the encoded *Vernonia galamenensis* fatty acid modifying enzyme. An example of a vector for high level expression of the instant *Vernonia galamenensis* fatty acid modifying enzymes in a bacterial host is provided (Example 6).

All or a portion of the nucleic acid fragments of the instant invention may also be used as probes for genetically and physically mapping the genes that they are a part of, and as markers for traits linked to expression of the instant fatty acid epoxidizing and desaturase enzymes. Such information may be useful in plant breeding in order to develop lines with desired phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1) :37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derive from the instant nucleic acid sequences may also be used for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred KB), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and Happy Mapping. For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods. Such information may be useful in plant breeding in order to develop lines with desired starch phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Composition of a cDNA Library; Isolation and Sequencing of cDNA Clones

A cDNA library representing mRNAs from developing seeds of *Vernonia galamenensis* that had just begun production of vernolic acid was prepared. The library was prepared in a Uni-ZAP™ XR vector according to the manufacturer's protocol (Stratagene Cloning Systems, La Jolla, Calif.). Conversion of the Uni-ZAP™ XR library into a plasmid library was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

EXAMPLE 2

Identification and Characterization of cDNA Clones

ESTs encoding *Vernonia galamenensis* fatty acid modifying enzymes were identified by conducting BLAST (Basic Local Alignment Search Tool; Altschul, S. F., et al., (1993) J. Mol. Biol. 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone vs1.05h08 revealed similarity of the protein encodes by the cDNA to, inter alia, a tomato fatty acid desaturase enzyme (EMBL Accession No. X94944; pLog=1.72) and a potato fatty acid desaturase enzyme (EMBL Accession No. X92847; pLog=0.52). The sequence of the entire cDNA insert in clone vs1.05h08 was determined and reevaluated by BLAST, yielding even higher pLog values vs. the potato fatty acid desaturase enzyme (X92847; pLog=228.04). SEQ ID NO: 1 shows the nucleotide sequence of the entire *Vernonia galamenensis* cDNA in clone vs1.05h08; the deduced amino acid sequence is shown in SEQ ID NO:2. Sequence alignments and BLAST scores and probabilities indicate that the instant nucleic acid fragment encodes a *Vernonia galamenensis* fatty acid desaturase.

The BLASTX search using the nucleotide sequence of clone vs1.02c07 revealed similarity of the protein encodes by the cDNA to, inter alia, a potato fatty acid desaturase enzyme (EMBL Accession No. X92847; pLog=2.08) and a soybean fatty acid desaturase enzyme (GenBank Accession No. L43921; pLog=1.49). The sequence of the entire cDNA insert in clone vs1.02c07 was determined and reevaluated by BLAST, yielding even higher pLog values vs. the potato (X9247; pLog=156.18) and soybean fatty acid desaturase enzymes (L43921; pLog=152.18). SEQ ID NO:3 shows the nucleotide sequence of the entire *Vernonia galamenensis* cDNA; the deduced amino acid sequence is shown in SEQ ID NO:4.

The deduced amino acid sequences from cDNA clones vs1.05h08 and vs1.02c07 were compared to the deduced amino acid sequences encoding (i) a know fatty acid desaturase from soybean (World Patent Publication No. WO94/11516) and (ii) a fatty acid hydroxylase from castor bean (van de Loo, F. J. et al. (1995) *Proc. Natl. Acad. Sci. U.S.A.* 92 (15):6743–6747) using the multiple sequence comparison program "Megalign" from the Lasargene™ software package (DNASTAR Inc., Madison, Wis.). The aligned sequences are shown in FIG. 1. All four sequences are related by eight very highly conserved residues that are apparently part of the binding site for the two iron cluster that is required in the active site of enzymes in this class (Shanklin, J. et al. (1994) *Biochemistry* 33:12787–12793). The cDNA insert in clone vs1.05h08 is about 70% similar to the known fatty acid desaturase from soybean, while the cDNA insert in vs1.02c07 is only 53.8% similar to this soybean fatty acid desaturase. This degree of divergence is similar to that observed between the fatty acid hydroxlyase from castor bean and the fatty acid desaturases. Thus, changes in a comparatively small number of amino acid residues in conserved regions of the protein are sufficient to alter the activity in this class of enzymes from one of introducing a double bond (i.e, a desaturase) to one of introducing an hydroxyl group (i.e., a hydroxylase).

The sequence of clone vs1.02c07 is also quite divergent from the castor bean fatty acid hydroxylase, sharing only 52.5% similar residues. The sequence of vs1.02c07 is therefore unique, but nonetheless related, to the class of enzymes which is known to contain enzymes capable of producing different modifications in the acyl chains of fatty acids. Sequence alignments, BLAST scores and probabilities and experimental data demonstrating a tissue-specific expression pattern (see Example 3) for the gene encoded by the cDNA clone vs1.02c07 indicate that the instant nucleic acid fragment comprising this clone encodes a *Vernonia galamenensis* fatty acid epoxidizing enzyme.

EXAMPLE 3

Tissue Specific Expression of the Fatty Acid Epoxidase

Expression of enzymes which produce unusual fatty acids has been shown to be specific for the storage organs in which these fatty acids are found (see World Patent Publication No. WO94/11516). Northern analysis of mRNA from developing leaves of *Vernonia galamenensis* was performed using the cDNA insert in vs 1.02c07 as a probe. Messenger RNA from leaves that were near full expansion (by comparison to other leaves just lower on the main stem) were removed and mRNA was prepared by standard methods well known in the art. The leaf mRNA, and a remaining sample of the developing seed mRNA that was used as template for the cDNA library from which the instant cDNA clones were obtained, was separated by denaturing agarose gel electrophoresis and blotted to a nylon membrane for hybridization to the probe.

The $^{32}$P-labeled probe based on the cDNA insert in vs1.02c07 was prepared by PCR amplification of the coding region of the cDNA using the nucleotide described in SEQ ID NO:7 as the 5' end primer and the nucleotide described in SEQ ID NO:8 as the 3' end primer. The product from PCR amplification was purified by isolation from an agarose gel and used as template for random primed labeling. The portion of cDNA clone vs1.05h08 encoding the peptide was similarly amplified using the nucleotides described in SEQ ID NOs:9 and 10 as the 5' and 3' primers, respectively, and the purified product used as probe template.

Both probes were hybridized to the Northern blots at 62° C. in 0.2× SSC overnight. Excess probe was removed by washing under the same stringency conditions and the blot was placed on photographic film for development.

The lane containing the seed mRNA produced an intense hybridization signal at about 1.9 kD when the coding region ovs1.02c07 was used as the probe, while no signal was visible in the lane containing the leaf-derived mRNA. Further exposure of the blot, such that the seed-derived signal was highly over exposed, still did not result in a visible signal in the lane containing the leaf-derived message. The coding region of vs1.05h08 hybridized to message from both developing seeds and from leaves.

The cDNA insert in vs1.02c07 is therefore not expressed in a *Vernonia galamenensis* tissue that does not produce epoxidized fatty acids, but is highly expressed in a tissue that does produce the modified fatty acid. The tissue-specific nature of its expression, its relationship to a known class of fatty acid modifying enzymes, and its divergence from enzymes in that class whose catalytic function has been demonstrated, all indicate that the cDNA insert in vs1.02c07 encodes the fatty acid epoxidizing enzyme from *Vernonia galamenensis*.

EXAMPLE 4

Expression of Chimeric Genes in Monocot Cells

The oil storing tissues of most grass seeds are the embryo and its attending tissues the scutellum and to some extent the aleurone. Promoter sequences such as those controlling expression of the storage proteins Globulin 1 (Belanger, S. C. and Kriz, A. L. (1989) *Plant Physiol.* 91:636–643) and Globuin 2 (Wallace, N. H. and Kriz, A. L. (1991) *Plant Physiol.* 95:973–975) are appropriate for the expression of chimeric genes in these tissues.

A chimeric gene comprising a cDNA encoding a *Vernonia galamenensis* fatty acid epoxidizing enzyme in sense orientation with respect to the maize Globulin 2 promoter that is located 5' to the cDNA fragment, and the Globulin 2 3' end that is located 3' to the cDNA fragment, can be constructed. The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the correctly designed expression vector.

Such expression vectors should include genetic sequence elements conferring an origin of replication for the plasmid in its host, a gene capable of conferring a selectable trait such as autotrophy or antibiotic tolerance to the host cell carrying the plasmid, and the promoter sequences for expression of desired genes in host plant cells. Further design features may include unique restriction endonuclease recognition sites between the elements of the plant gene promoter elements to allot convenient introduction genes to be controlled by those elements.

The chimeric genes constructed as above can then be introduced into corn cells by the following procedure. Immature worn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5M solution) and spermidine free base (20 μL of a 1.0M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

EXAMPLE 5

Expression of Chimeric Genes in Dicot Cells

The *Vernonia galamenensis* fatty acid epoxidizing enzyme can be expressed in cells of dicots that normally produce storage lipid by the construction of appropriate chimeric genes followed by stable introduction of those genes into the host plant. An example of this method is the seed specific expression of the *Vernonia galamenensis* fatty acid epoxidizing enzyme in soybean.

The plasmid pKS18HH, containing chimeric genes to afford expression of the selectable marker hygromycin phosphotransferase in certain bacteria and in plant cells, was constructed from the following genetic elements: i) T7 Promoter plus Shine-Delgarno ribosome binding site/ hygromycin phosphotransferase (HPT)/T7 Terminator Sequence, ii) 35S promoter from cauliflower mosaic virus (CaMV)/hygromycin phosphotransferase (HPT)/Nopaline Synthase (NOS from *Agrobacterium tumefaciens* T-DNA, and iii) pSP72 plasmid vector (from Promega Biotech) with beta-lactamase coding region (ampicillin resistance gene) removed. The hygromycin phosphotransferase gene was amplified by PCR from *E. coli* strain W677, which contained a Klebsiella-derived plasmid pJR225. Starting with the pSP72 vector, the elements were assembled into a single plasmid using standard cloning methods (Maniatis).

Plasmid pKS18HH thus contains the T7 promoter/HPT/T7 terminator cassette for expression of the HPT enzyme in certain strains of *E. coli,* such as NovaBlue(DE3) (Novagen), that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. The components that comprise this cassette are (i) the 35S promoter from Cauliflower Mosaic Virus (35S; Odell et al.(1985) *Nature* 313:810–812), (ii) the hygromycin phosphotransferase gene from plasmid pJR225 (HPT; from *E. coli;* Gritz et al.(1983) *Gene* 25:179–188) and the 3' region of the nopaline synthase gene from the T-DNA of the Ti plasmid of *Agrobacterium tumefaciens* (NOS). The two expression systems incorporated into plasmid pKS18HH allow selection for growth in the presence of hygromycin, and is therefore used as a means of identifying cells that contain the plasmid in both bacterial and plant systems. pKS18HH also contains three unique restriction endonuclease suitable for the cloning other chimeric genes into this vector.

A plasmid for expression the cDNA encoding the *Vernonia galamenensis* fatty acid epoxidizing enzyme under control of the soybean beta-conglycinin promoter (Beachy et al.,(1985) *EMBO J.* 4:3047–3053) was constructed. The construction of this vector was facilitated by the use of plasmids pCW109 and pML18, both of which have been described (see World Patent Publication No. WO94/11516).

A unique Not I site was introduced into the cloning region between the beta-conglycinin promoter and the phaseolin 3' end in pCW109 by digestion with Nco I and Xba I followed by removal of the single stranded DNA ends with mung bean exonuclease. Not I linkers (New England Biolabs; catalog no. NEB 1125) were ligated into the linearized plasmid to produce plasmid pAW35. The single Not I site in pML18 was destroyed by digestion with Not I, filling in the single stranded ends with dNTP's and Klenow fragment of DNA polymerase, and re-ligation of the linearized plasmid. The modified pML18 was then digested with Hind III and treated with calf intestinal phosphatase.

The beta-conglicinin/Not I/phaseolin expression cassette in pAW35 was removed by digestion with Hind III, and the 1.79 kB fragment was isolated by agarose gel electrophoresis. The isolated fragment was ligated into the modified and linearized pML18 construction described above. A clone with the desired orientation was identified by digestion with Not I and Xba I to release a 1.08 kB fragment, indicating that the orientation of the beta-conglycinin transcription unit was the same as the selectable marker transcription unit. The resulting plasmid was given the name pBS19

Hind III is one of the unique cloning sites available in pKS18HH. To assemble the final expression cassette, pBS19 and pKS18HH were both digested with Hind III. The beta-conglycinin-containing fragment from pBS19 was isolated by gel electrophoresis and ligated into the digested pKS18HH which had been treated with calf alkaline phosphatase. The resulting plasmid was named pRB20.

The PCR product amplified from clone vs1.02c07 (described in Example 3 above) was digested with Not I to cleave the Not I sites designed into the PCR primers. Plasmid pRB20 was also digested with Not I. After phosphatase treatment of the linearized pRB20, the Not I-digested vs1.02c07 product was ligated into pRB20 and the ligation mixture used to transform *E. coli* strain DE3. Colonies were selected and grown in liquid media for preparation of plasmid DNA. Digestion of the plasmid DNA with Xmn I released a fragment of 0.4 kB when the coding sequence of vs1.02c07 was oriented in the sense direction relative to the beta-conglycinin promoter. The selected clone was designated pRVF7 and was used to produce plasmid DNA for stable transformation of soybean.

Soybean embryos may the be transformed with the expression vector comprising sequences encoding a *Vernonia galamenensis* fatty acid epoxidizing enzyme such as pRFV7. To induce somatic embryos, cotyledons, 3–5 mm in length dissected from surface sterilized, immature seeds of the soybean cultivar A2872, can be cultured in the light or dark at 26° C. on an appropriate agar medium or 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No.

4,945,050). A Du Pont Biolistic™ PDS1000/HE instrument (helium retrofit) can be used for these transformations.

To 50 mL of a 60 mg/mL 1 mm gold particle suspension is added (in order): 5 mL DNA (1 mg/mL), 20 ml spermidine (0.1M), and 50 mL CaCl2 (2.5M). The particle preparation is then agitated for three minutes, spun in a microfuge for 10 seconds and the supernatant removed. The DNA-coated particles are then washed once in 400 mL 70% ethanol and resuspended in 40 m L of anhydrous ethanol. The DNA/particle suspension can be sonicated three times for one second each. Five mL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos. Immature embryos at this stage produce storage products, including storage lipids that are similar in composition to zygoti embryos at a similar stage of development. Analysis of the storage product composition of transgenic, somatic embryos allows the identification of successful transgenic events and is predictive of the composition of storage products in the sexually derived seeds of plants recovered from the somatic embryos (see World Patent Publication No. WO94/11516).

Whole plants containing the integrated transgene may be obtained by maturation and germination of individual somatic embryos on appropriate media followed by transfer to soil.

EXAMPLE 6

Expression of Chimeric Genes in Microbial Cells

The cDNAs encoding the instant *Vernonia galamenensis* fatty acid epoxidizing or desaturase enzymes can be inserted into the T7 *E. coli* expression vector pET24d (Novagen). For example, plasmid DNA containing a cDNA may be appropriately digested to release a nucleic acid fragment encoding the *Vernonia galamenensis* fatty acid epoxidizing enzyme. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenol/chloroform as described above. The prepared vector pET24d and fragment can then be ligated at 16° C. for 15 hours followed by transformation into DH5 electrocompetent cells (GIBCO BRL). Transformants can be selected on agar plates containing 2xYT media and 50 μg/mL kanamycin. Transformants containing the gene are then screened for the correct orientation with respect to pET24d T7 promoter by restriction enzyme analysis.

Clones in the correct orientation with respect to the T7 promoter can be transformed into BL21(DE3) competent cells (Novagen) and selected on 2xYT agar plates containing 50 μg/ml kanamycin. A colony arising from this transformation construct can be grown overnight at 30° C. in 2xYT media with 50 μg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment encoding a *Vernonia galamenensis* fatty acid desaturase comprising a member selected from the group consisting of:
    (a) an isolated nucleic acid fragment encoding the amino acid sequence of SEQ ID NO:2 or an enzymatically active fragment thereof; and
    (b) an isolated nucleic acid fragment which will hybridize under stringent conditions to a nucleotide sequence encoding SEQ ID NO:2.

2. The isolated nucleic acid fragment of claim 1 wherein the nucleotide sequence of the fragment is set forth in SEQ ID NO:1.

3. A chimeric gene comprising the nucleic acid fragment of claim 1 operably linked to suitable regulatory sequences.

4. A transformed host cell comprising the chimeric gene of claim 3.

5. An isolated nucleic acid fragment encoding a *Vernonia galamenensis* fatty acid epoxidizing enzyme comprising a member selected from the group consisting of:
    (a) an isolated nucleic acid fragment encoding the amino acid sequence of SEQ ID NO:4 or an enzymatically active fragment thereof; and
    (b) an isolated nucleic acid fragment which will hybridize under stringent conditions to a nucleotide sequence encoding SEQ ID NO:4.

6. The isolated nucleic acid fragment of claim 5 wherein the nucleotide sequence of the fragment is set forth in SEQ ID NO:3.

7. A chimeric gene comprising the nucleic acid fragment of claim 5 operably linked to suitable regulatory sequences.

8. A transformed host sell comprising the chimeric gene of claim 7.

9. A method of altering the level of expression of a *Vernonia galamenensis* fatty acid modifying enzyme in a host sell comprising:
    (a) transforming a host cell with the chimeric gene of claim 3 or the chimeric gene of claim 7; and
    (b) growing the transformed host cell produced in step (a) under conditions that are suitable for expression of the chimeric gene
wherein expression of the chimeric gene results in production of altered levels of a *Vernonia galamenensis* fatty acid modifying enzyme in the transformed host cell.

10. A method of producing a *Vernonia galamenensis* fatty acid modifying enzyme comprising the following steps:
    (a) transforming a microbial host cell with the chimeric gene of claim 3 or claim 7; and
    (b) growing the transformed microbial cells obtained from step (a) under conditions that result in expression of the *Vernonia galamenensis* fatty acid modifying enzyme.

11. A method of obtaining a nucleic acid fragment encoding a *Vernonia galamenensis* fatty acid modifying enzyme or an enzymatically active fragment thereof comprising:
    (a) probing a *Vernonia galamenensis* cDNA or genomic DNA library with the nucleic acid fragment of claim 1 or claim 5;
    (b) identifying a DNA clone that hybridizes under stringent conditions to the nucleic acid fragment of claim 1 or claim 5; and
    (c) isolating the DNA clone identified in step (b);
wherein the isolated DNA clone of step (c) comprises a nucleic acid fragment encoding a *Vernonia galamenensis* fatty acid modifying enzyme or an enzymatically active fragment thereof.

12. A method of obtaining a nucleic acid fragment encoding a fragment of a *Vernonia galamenensis* fatty acid modifying enzyme comprising:
    (a) synthesizing an oligonucleotide primer comprising a fragment of at least 12 bases of the nucleotide sequence of SEQ ID NO:1 or SEQ ID NO:3; and
    (b) amplifying a *Vernonia galamenensis* cDNA insert present in a cloning vector using the oligonucleotide primer of step (a) and an oligonucleotide primer comprising a fragment of at least 12 bases of the nucleotide sequence of the cloning vector
wherein the amplified nucleic acid fragment encodes a fragment of a *Vernonia galamenensis* fatty acid modifying enzyme.

13. The product of the method of claim 11.

14. The product of the method of claim 12.

15. An isolated nucleic acid fragment complementary to the nucleic acid fragment of claim 1.

16. An isolated nucleic acid fragment complementary to the nucleic acid fragment of claim 5.

17. The method of claim 12 wherein the oligonucleotide primers are 12–15 bases in length.

* * * * *